(12) United States Patent
Kato et al.

(10) Patent No.: US 9,448,360 B2
(45) Date of Patent: Sep. 20, 2016

(54) OPTICAL ELEMENT

(71) Applicant: CITIZEN HOLDINGS CO., LTD., Tokyo (JP)

(72) Inventors: Seiko Kato, Saitama (JP); Masafumi Ide, Saitama (JP)

(73) Assignee: CITIZEN HOLDINGS CO., LTD., Tokyo (JP)

( * ) Notice: Subject to any disclaimer, the term of this patent is extended or adjusted under 35 U.S.C. 154(b) by 0 days.

(21) Appl. No.: 14/655,127

(22) PCT Filed: Dec. 25, 2013

(86) PCT No.: PCT/JP2013/084692
§ 371 (c)(1),
(2) Date: Jun. 24, 2015

(87) PCT Pub. No.: WO2014/104105
PCT Pub. Date: Jul. 3, 2014

(65) Prior Publication Data
US 2015/0323734 A1 Nov. 12, 2015

(30) Foreign Application Priority Data
Dec. 28, 2012 (JP) ................................. 2012-288590

(51) Int. Cl.
*G02B 6/44* (2006.01)
*G02B 6/024* (2006.01)
*G02B 6/126* (2006.01)
*G02B 6/122* (2006.01)
(Continued)

(52) U.S. Cl.
CPC ................. *G02B 6/024* (2013.01); *G02B 6/12* (2013.01); *G02B 6/122* (2013.01); *G02B 6/126* (2013.01); *G02B 6/138* (2013.01); *G02B 2006/12171* (2013.01); *G02F 1/1326* (2013.01)

(58) Field of Classification Search
CPC ........................................................ G02B 6/00
USPC .......................... 385/100, 102, 103; 349/193
See application file for complete search history.

(56) References Cited

U.S. PATENT DOCUMENTS

| 5,586,205 A | 12/1996 | Chen et al. |
|---|---|---|
| 2003/0103708 A1 | 6/2003 | Galstian et al. |

(Continued)

FOREIGN PATENT DOCUMENTS

| JP | 2006-162678 A | 6/2006 |
|---|---|---|
| JP | 2008-530766 A | 8/2008 |
| WO | 2012/114164 A1 | 8/2012 |

OTHER PUBLICATIONS

International Search Report for PCT/JP2013/084692, Feb. 10, 2014.
(Continued)

*Primary Examiner* — Lucy Chien (57) ABSTRACT

Provided is an optical element having an optical waveguide region that can propagate azimuthally polarized light or radially polarized light while maintaining the direction of polarization. The optical element has a resin layer and an optical waveguide region that is formed in the resin layer and guides light in the lengthwise direction of the resin layer. Liquid crystal molecules are oriented in an approximately radiating shape in a cross section perpendicular to the lengthwise direction in the optical waveguide region, and the refractive index of the optical waveguide region is greater than that of the resin layer.

4 Claims, 11 Drawing Sheets (51) Int. Cl.
G02B 6/138 (2006.01)
G02B 6/12 (2006.01)
G02F 1/13 (2006.01)

(56) References Cited

U.S. PATENT DOCUMENTS

2005/0169590 A1  8/2005  Alkeskjold
2009/0027872 A1  1/2009  Debije et al.
2009/0044861 A1  2/2009  Debije et al.

OTHER PUBLICATIONS

Stump, A. et al., "Optical waveguides structured with photoaligning polymers", Optics Letters, vol. 30, No. 11, Jun. 1, 2005, pp. 1333-1335.

R. Romaniuk, "Capillary optical fiber—design, fabrication, characterization and application", Bulletin of the Polish Academy of Sciences Technical Sciences, Jun. 2008, vol. 56, No. 2, pp. 87-102.
R. Romaniuk, "Two classes of capillary optical fibers: refractive and photonic", Nov. 6, 2008, Proc. of SPIE vol. 7124 71240D.
Written Opinion of the International Searching Authority for PCT/JP2013/084692, Feb. 10, 2014.
European Patent Office, Extended European Search Report for EP Patent Application No. 13867698.6, Jul. 26, 2016.
M. Trotta et al., "All Optical Tunable Nematic Liquid Crystal Waveguide", Molecular Crystals and Liquid Crystals, May 30, 2012, vol. 558, No. 1, pp. 204-208.
R. J. Black et al., "Radially Anisotropic Lightguide Mode Selector", Electronics Lettrs, Oct. 10, 1985, vol. 21, No. 21, pp. 987-989.
A. E. Vasdekis et al., "Liquid Crystal Optofluidics", SPIE, Oct. 11, 2012, vol. 8475, pp. 847507-847507.
D. C. Zografopoulos et al., "Guided-wave liquid-crystal photonics", Lab Chip, 2012, Jun. 14, 2012, vol. 12, No. 19, pp. 3598-3610.

OPTICAL ELEMENT

TECHNICAL FIELD

The present invention relates to an optical element including a resin layer and an optical waveguide region that is formed in the resin layer.

BACKGROUND

Patent Literature 1 describes an optical fiber system in which optical transmission properties are controlled by applying a magnetic field to a filled liquid crystal to change the orientation of the liquid crystal in an optical fiber including a liquid-crystal-filled optical fiber which is formed of a hollow fiber filled with the liquid crystal.

Non Patent Literature 1 describes a capillary optical fiber including an optical core having a ring shape and a high refractive index around an air hole, an optical clad having a low refractive index, and a covering layer having a high refractive index.

CITATION LIST

Patent Literature

Patent Literature 1: Japanese Laid-open Patent Publication No. 2006-162678

Non Patent Literature

Non Patent Literature 1: R. ROMANIUK, "Capillary optical fiber-design, fabrication, characterization and application", BULLETIN OF THE POLISH ACADEMY OF SCIENCES TECHNICAL SCIENCES, 2008, Vol. 56, No. 2, p. 87-102

SUMMARY

A conventional optical waveguide made of a resin material includes isotropy or anisotropy in which orientation occurs only in a specific one direction. Therefore, it is impossible to propagate radially polarized light or azimuthally polarized light in such an optical waveguide while maintaining a polarization direction. The term "radially polarized light" as used herein refers to light of which the polarization direction is radially distributed in a radial direction in a plane perpendicular to a travelling direction. The term "azimuthally polarized light" refers to light of which the polarization direction is distributed in a circumferential direction in a plane perpendicular to a travelling direction.

An optical waveguide with a radial orientation structure can be used for radially polarized light or azimuthally polarized light. However, it is difficult to easily produce such an optical waveguide. Thus, an objective of the present invention is to provide an optical element including an optical waveguide region that can propagate radially polarized light or azimuthally polarized light while maintaining the direction of polarization.

Provided is an optical element including a resin layer, and an optical waveguide region that is formed in the resin layer and guides light in the lengthwise direction of the resin layer, wherein liquid crystal molecules are oriented in an approximately radiating shape in a cross section perpendicular to the lengthwise direction in the optical waveguide region, and the refractive index of the optical waveguide region is greater than that of the resin layer.

Preferably, the above optical element further includes a tubular space having an approximately circular cross section formed in the resin layer, wherein the optical waveguide region is formed so as to be in contact with the tubular space, and liquid crystal molecules are oriented in an approximately radiating shape along the radial direction of the approximately circular cross section in the optical waveguide region.

The above optical element can propagate radially polarized light or azimuthally polarized light while maintaining the direction of polarization.

BRIEF DESCRIPTION OF THE DRAWINGS

FIGS. 8(A) and (B) are views for explaining the conditions of the waveguide simulation of the optical element 10;

FIGS. 11(A) and (B) are views for explaining an SPR sensor to which the optical element 10 is applied.

DESCRIPTION

Hereinafter, with reference to the drawings, an optical element will be explained in detail. However, it should be noted that the technical scope of the present invention is not limited to embodiments thereof and includes the invention described in claims and equivalents thereof.

Figure 1:
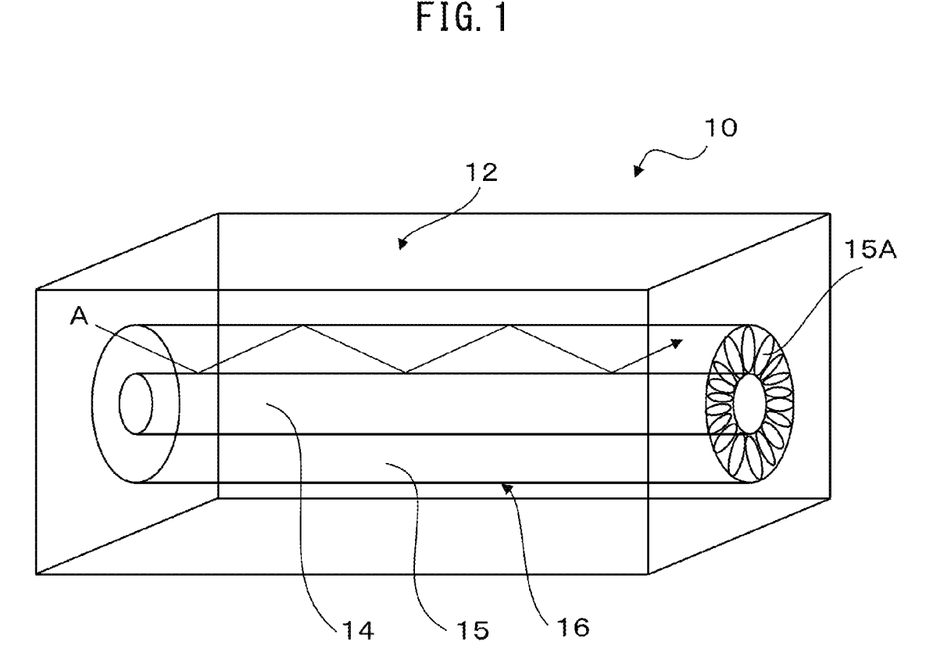
FIG. 1 is a schematic view of an optical element 10.

FIG. 1 is a schematic view of an optical element 10. The optical element 10 includes a resin layer 12 as a clad portion of an optical waveguide region. In the optical element 10, an acrylic resin is used as the resin layer 12. A cavity 14 which is a tubular space having an approximately circular cross section is formed in the interior of the resin layer 12. The term "approximately circular shape" refers to a shape without any sharp protruding portion or any depression, as included in a rectangular shape, in which the rate of a difference between maximum and minimum diameters to the maximum diameter is, for example, 10% or less.

In addition, the optical element 10 includes a liquid crystal region 15 formed, as a core portion of the optical waveguide region, in a portion (in the vicinity of a boundary) of the resin layer 12 which is in contact with the cavity 14. In the optical element 10, a P-type liquid crystal is used as the liquid crystal. In the liquid crystal region 15, liquid crystal molecules are oriented in an approximately radiating shape along the radial direction of the cavity 14 having an approximately circular cross section. In FIG. 1, the orientation of the liquid crystal molecules is represented by a large number of ellipses 15A that are placed in an approximately radiating shape in a radial direction in an approximately circular cross section around the cavity 14. The term "approximately radiating shape" refers to the state of spreading, as a whole, from the cavity 14 in the center toward the outside of the resin layer 12. Therefore, the liquid crystal molecules need not be strictly radially oriented in the whole liquid crystal region 15.

In the optical element 10, the liquid crystal region 15 functions as an optical waveguide region, and can propagate light therein. Since the liquid crystal region 15 has a greater refractive index than the resin layer 12, there is a difference between the refractive indices of the resin layer 12 and the liquid crystal region 15. Accordingly, when light is incident into the liquid crystal region 15, light from the liquid crystal region 15 toward the external resin layer 12 at a small incidence angle is totally reflected by a boundary surface 16 between the liquid crystal region 15 and the resin layer 12.

Similarly, since the liquid crystal region 15 has a greater refractive index than the internal cavity 14, there is a difference between the refractive indices of the cavity 14 and the liquid crystal region 15. Accordingly, light from the liquid crystal region 15 toward the internal cavity 14 at a small incidence angle is also totally reflected by a boundary surface between the liquid crystal region 15 and the cavity 14. Since light is propagated in the liquid crystal region 15 as described above (see the arrow A in FIG. 1), the optical element 10 can confine light in the liquid crystal region 15.

Actually, the refractive index is decreased as the distance from the boundary surface with the cavity 14 is increased in the radial direction due to the concentration gradient of the liquid crystal molecules in the liquid crystal region 15. The optical element 10 can be used as a GI (graded-index) type waveguide due to the distribution of the refractive index.

The boundary surface 16 between the resin layer 12 and the liquid crystal region 15 is illustrated for purposes of explanation in FIG. 1. However, the boundary surface 16 may not be actually clearly defined. However, light propagated in the liquid crystal region 15 is reflected before arriving at a region with a lower refractive index outside the liquid crystal region 15, and is thereby propagated in the liquid crystal region 15.

Figure 2:
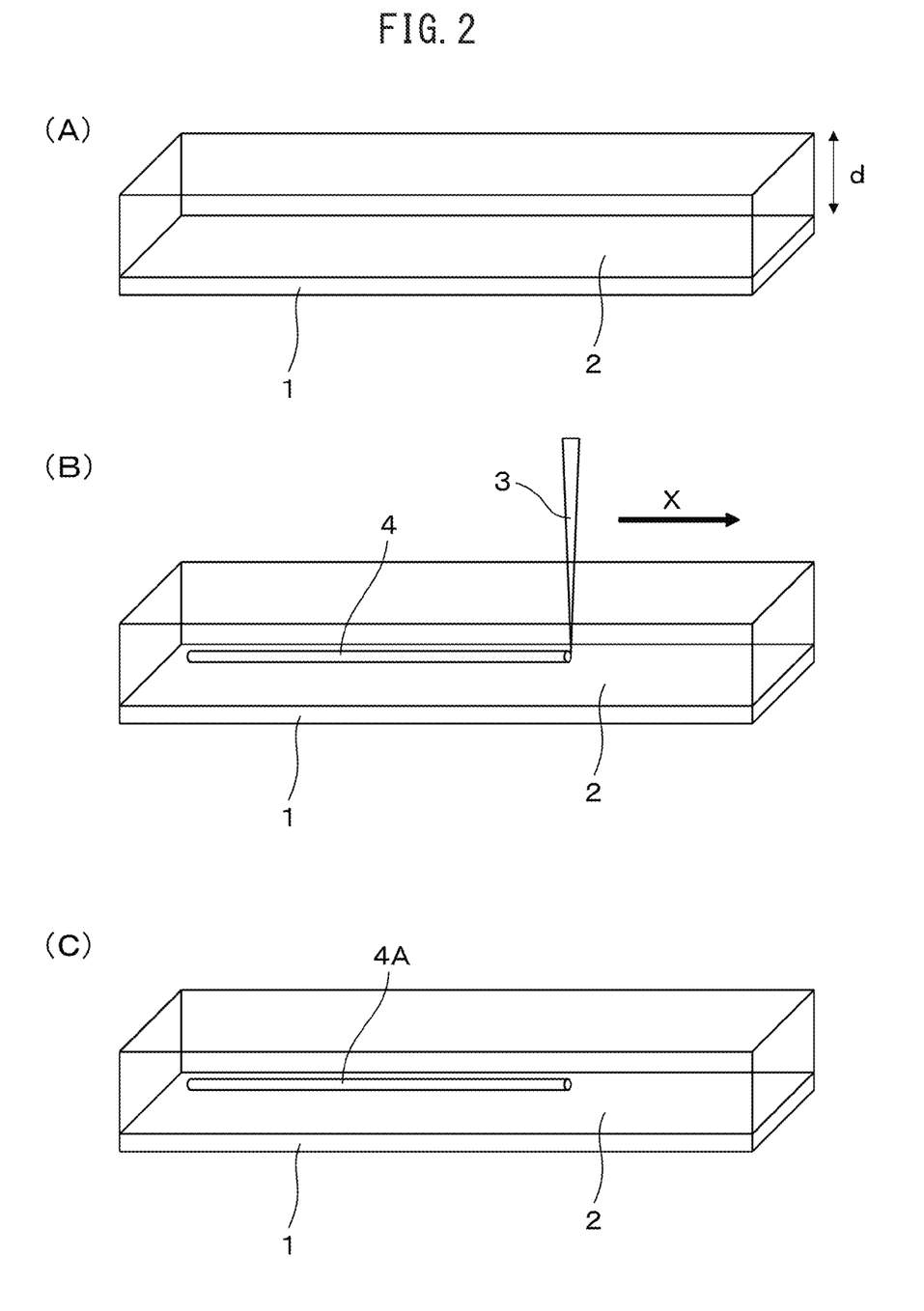
FIGS. 2(A) to (C) are schematic views for explaining a method for producing the optical element 10.
Figure 3:
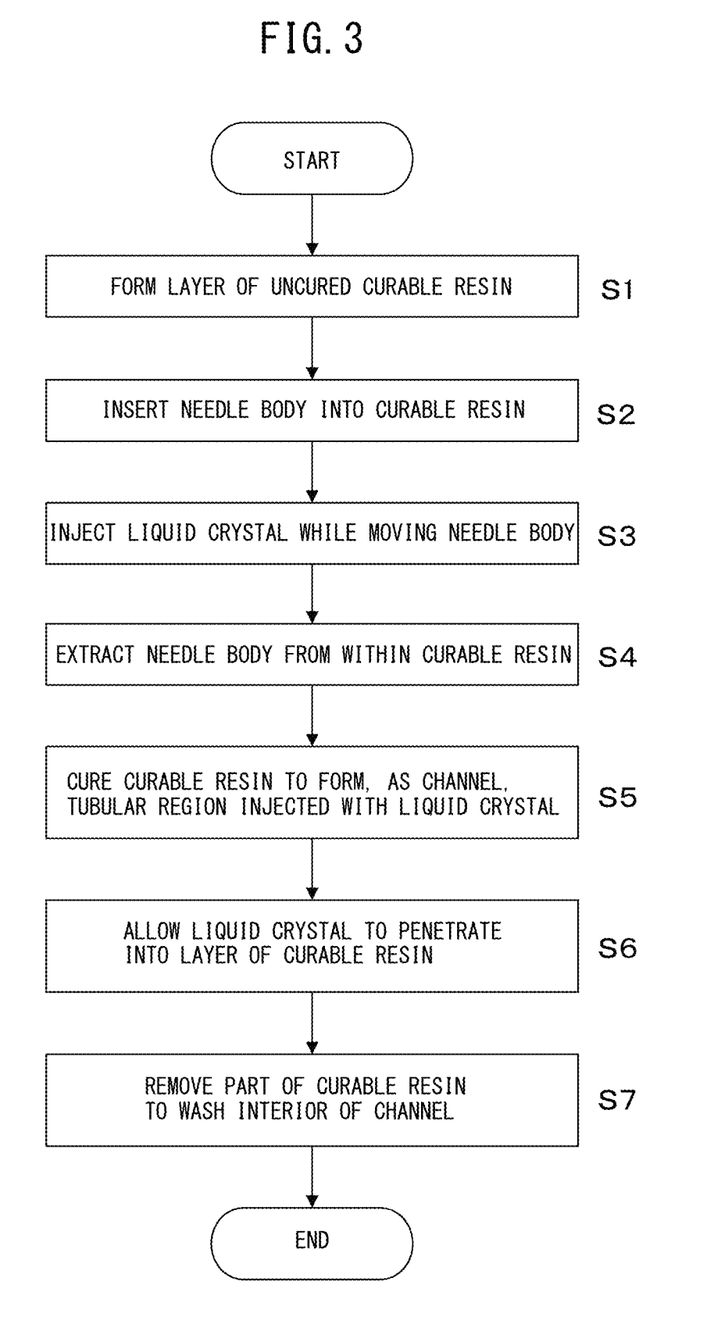
FIG. 3 is a flowchart representing the method for producing the optical element 10.

FIG. 2(A) to FIG. 2(C) are schematic views for explaining a method for producing the optical element 10. FIG. 3 is a flowchart representing the method for producing the optical element 10. Each step in the production method will be explained with reference to FIG. 1 to FIG. 3.

First, as illustrated in FIG. 2(A), a substrate 1 is prepared, and an uncured layer of a curable resin 2 is formed on the substrate 1 (S1). The layer corresponds to the resin layer 12 in FIG. 1. Since the curable resin 2 in an uncured state has flowability, a frame (not illustrated) surrounding a perimeter is prepared, and the curable resin 2 is injected into the frame. In this example, an acrylic resin which is an ultraviolet cured resin is used as the curable resin 2. However, a thermosetting resin may also be used as the curable resin 2. When the diameter of the cavity 14 in FIG. 1 is set at around several-hundred μm, the thickness d of the curable resin 2 may be around 1000 μm.

Subsequently, a needle (needle body) 3 that can inject a liquid crystal is inserted into the curable resin 2 (S2). The needle 3 has a hollow shape tapering down toward a tip thereof, such as the shape of an injection needle, and includes an opening (not illustrated) in the tip. In this case, a depth to which the needle 3 is inserted is set at, for example, around half of the thickness d of the curable resin 2. Alternatively, a needle in which the opening is disposed on a side in the vicinity of a tip of the needle may be used.

Then, a liquid crystal 4 is injected in a tubular shape into the curable resin 2 via the needle 3 while moving the needle 3 (S3), as illustrated in FIG. 2(B). In this example, a P-type liquid crystal is used as the liquid crystal 4. For example, in order to form a channel with a straight line shape, the needle 3 is moved in parallel along an X direction illustrated in FIG. 2(B). In addition, the liquid crystal 4 is injected from the opening in the tip of the needle 3 into the layer of the curable resin 2 by pressurization from the upper portion of the needle 3 while moving the needle 3. In the layer of the curable resin 2, the liquid crystal 4 has an approximately circular cross section perpendicular to the X direction due to surface tension.

After the injection of the liquid crystal 4, the needle 3 is extracted from the curable resin 2 (S4). In this case, the curable resin 2 is not yet cured, and therefore, a hole opened in the curable resin 2 by the needle 3 is closed by extracting the needle 3. As a result, the liquid crystal 4 is confined within the curable resin 2 and placed in the tubular shape.

In addition, the curable resin 2 is cured by irradiation with ultraviolet rays to confine the liquid crystal 4 within the curable resin 2. As a result, a portion, in which the liquid crystal 4 is present, is formed as a channel 4A for a liquid crystal (S5) as illustrated in FIG. 2(C). When a thermosetting resin is used as the curable resin 2, the curable resin 2 is cured by heating. In such a manner, the channel 4A having an approximately circular cross section is formed in a tubular region injected with the liquid crystal 4.

The liquid crystal 4 may penetrate into the curable resin 2 even before the curable resin 2 is cured. However, the liquid crystal 4 remains within the channel 4A immediately after the curing. Thus, the curable resin 2 is left untouched for a predetermined time to complete the penetration of the liquid crystal 4 into the layer of the curable resin 2 (S6). The liquid crystal 4 is diffused into the resin on the boundary surface between the liquid crystal 4 and the curable resin 2 with a lapse of time due to the concentration gradient, and the liquid crystal molecules are oriented in the direction of the diffusion as illustrated in FIG. 1. The chains of the resin are fixed by the curing, and the liquid crystal molecules enter the chains, to thereby obtain the region (liquid crystal region 15 in FIG. 1) in which the liquid crystal molecules are oriented in an approximately radiating shape around the channel 4A. When the liquid crystal 4 disappears from the channel 4A, the region of the channel 4A becomes the cavity 14 in FIG. 1.

When the liquid crystal 4 is completely confined in the curable resin 2, it takes several days before the penetration into the resin occurs depending on the kind of the liquid crystal 4. In contrast, when the hole formed by the needle 3 is not closed but remains open or when a hole is intentionally bored in the layer of the curable resin 2 to expose the liquid crystal 4 to the outside air, the liquid crystal 4 more quickly penetrates into the resin.

When the liquid crystal 4 remains in the channel 4A even after a lapse of predetermined time, a part of the curable resin 2 is removed to extract the liquid crystal 4 confined within the curable resin 2. Even when the channel 4A becomes hollow, a part of the curable resin 2 is removed to wash the interior of the channel 4A (S7). By the above steps, the cavity 14 and the liquid crystal region 15 in FIG. 1 are generated in the layer of the curable resin 2 to obtain the optical element 10 in FIG. 1.

It was found that the optical element 10 in FIG. 1 is obtained by using an acrylic resin and a P-type liquid crystal as the curable resin 2 and the liquid crystal 4, respectively, as described above and executing each step in FIG. 3. However, there may also be a combination of a resin and a liquid crystal, in which it is impossible to form the channel 4A with an approximately circular shape or the liquid crystal is not radially diffused into the resin. For example, the injected liquid crystal 4 may rise to the surface of the resin layer depending on the viscosity of the curable resin 2 or on a difference between the densities of the curable resin 2 and the liquid crystal 4. The liquid crystal 4 is often a mixture including plural compounds and has a diffusion coefficient varying according to the components. Therefore, it is necessary to select a combination of the curable resin 2 and the liquid crystal 4, in which the liquid crystal 4 can be injected in a tubular shape into the curable resin 2 and the liquid crystal 4 is diffused into the curable resin 2 and oriented in an approximately radiating shape, depending on the viscosity and the densities.

Since the penetration of the liquid crystal 4 occurs even after curing the curable resin 2 in the step S6 in FIG. 3, the optical element 10 may be obtained even by injecting the liquid crystal into the cavity already formed in the resin. Thus, another method for producing the optical element 10 is also explained.

In this method, first, a resin layer, in which a cavity having an approximately circular cross section is pre-formed, is prepared. In addition, a needle is inserted into the resin, a liquid crystal is injected into the cavity, and the needle is extracted. Then, steps similar to S6 and S7 in FIG. 3 are performed. In other words, the liquid crystal is allowed to penetrate into the resin for predetermined time, a part of the resin layer is then removed, and the interior of the cavity into which the liquid crystal was injected is washed. In the above steps, the optical element 10 is also obtained.

Even when it is impossible to form a circular channel by the production method of FIG. 3, some combinations of resins and liquid crystals can be used in the other production method described above. For example, when an epoxy resin is used as the curable resin 2, it is impossible to form a channel of a liquid crystal by the production method of FIG. 3. However, if a liquid crystal is injected into a channel already formed in a cured epoxy resin, the liquid crystal may be diffused into the resin and thereby result in an approximately radial orientation. Accordingly, the material of the resin layer 12 of the optical element 10 may also be, for example, another ultraviolet cured resin such as an epoxy resin, or a thermosetting resin such as a urea resin, a melamine resin, or a phenolic resin.

An experiment in which liquid crystal molecules were confirmed to be oriented in an approximately radiating shape in a liquid crystal region 15 will be explained below. In this experiment, an acrylic resin was used as the curable resin 2 in FIG. 2(A) to FIG. 2(C), and MLC-7018 and MDA-003461 which were P-type liquid crystals manufactured by Merck were used as the liquid crystal 4. In addition, the P-type liquid crystals were dispensed in straight line form into acrylic resin layers by the production method of FIG. 3.

The refractive index of the acrylic resin used in the experiment is 1.50, and the refractive indices of the P-type liquid crystal MLC-7018 manufactured by Merck are 1.55 as an extraordinary refractive index ne and 1.47 as an ordinary refractive index no. In this case, since the extraordinary refractive index ne is greater than the refractive index of the acrylic resin, radially polarized light which is polarized light parallel to the ne direction of liquid crystal molecules oriented in an approximately radiating shape is propagated.

Similarly, when the P-type liquid crystal MDA-003461 manufactured by Merck is used, the extraordinary and ordinary refractive indices ne and no of the liquid crystal are 1.77 and 1.54, respectively. Since these indices are greater than the refractive index of the acrylic resin of 1.50, both eigenpolarizations of extraordinary and ordinary rays have light confinement effects according to the orientation of the liquid crystal. Therefore, radially polarized light or azimuthally polarized light can be propagated.

Figure 4:
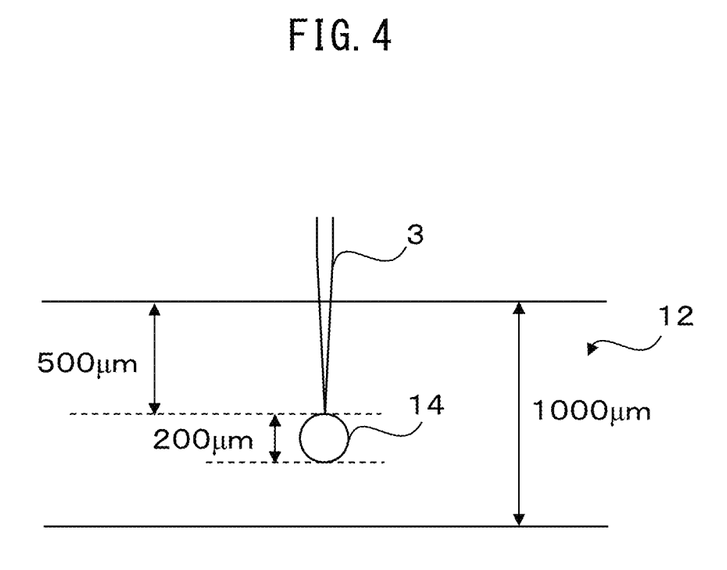
FIG. 4 is a schematic view for explaining the formation location and size of the cavity 14.

FIG. 4 is a schematic view for explaining the formation location and size of the cavity 14 formed in the experiment. In the experiment, the thickness of the resin layer 12 was set at 1000 μm, and the needle 3 was inserted to a depth of 500 μm in the resin layer 12. In addition, a dispensing pressure of 10 kPa was applied while moving the needle 3 at a speed of 20 mm/sec in straight line form along the surface direction of the resin layer 12, and thereby each P-type liquid crystal was dispensed so as to form the cavity 14 having an approximately circular cross section with a diameter of 200 μm.

In addition, a channel was formed by curing the resin layer 12 with ultraviolet rays after extracting the needle 3. Such two resin layers 12 were prepared. An opening was formed in the formed channel in one of the resin layers 12, while the internal liquid crystal remained completely encapsulated in the other resin layer 12. Then, the resin layers 12 were left to stand for several days to allow the liquid crystals to penetrate into the resin layers 12. In the experiment, the diameter of the channel (cavity 14) is greater than that in the case of use as an optical element.

Figure 5:
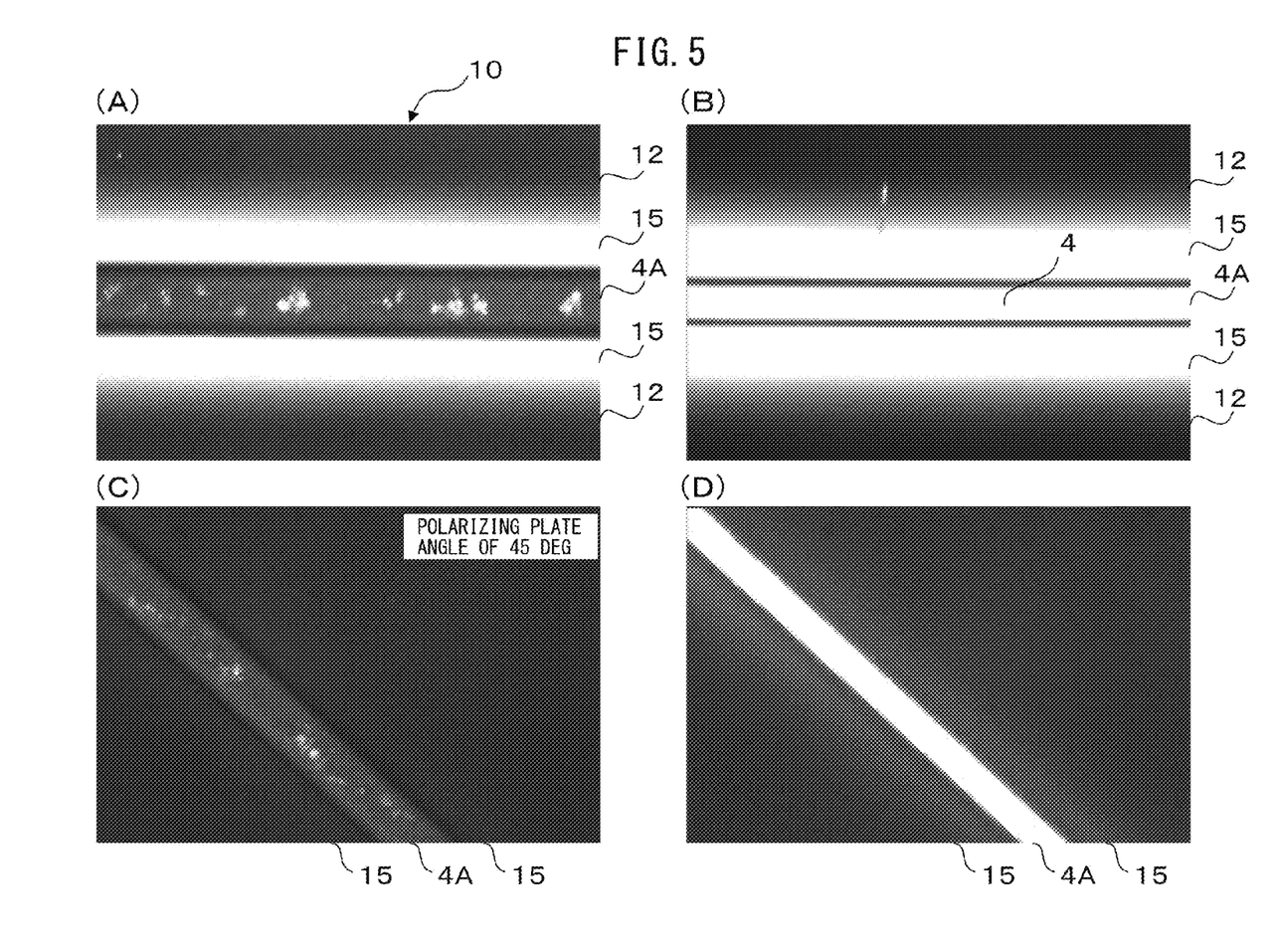
FIGS. 5(A) to (D) are photographs of a plane, observed by a polarizing microscope, of the optical element 10 parallel to the lengthwise direction thereof.
Figure 6:
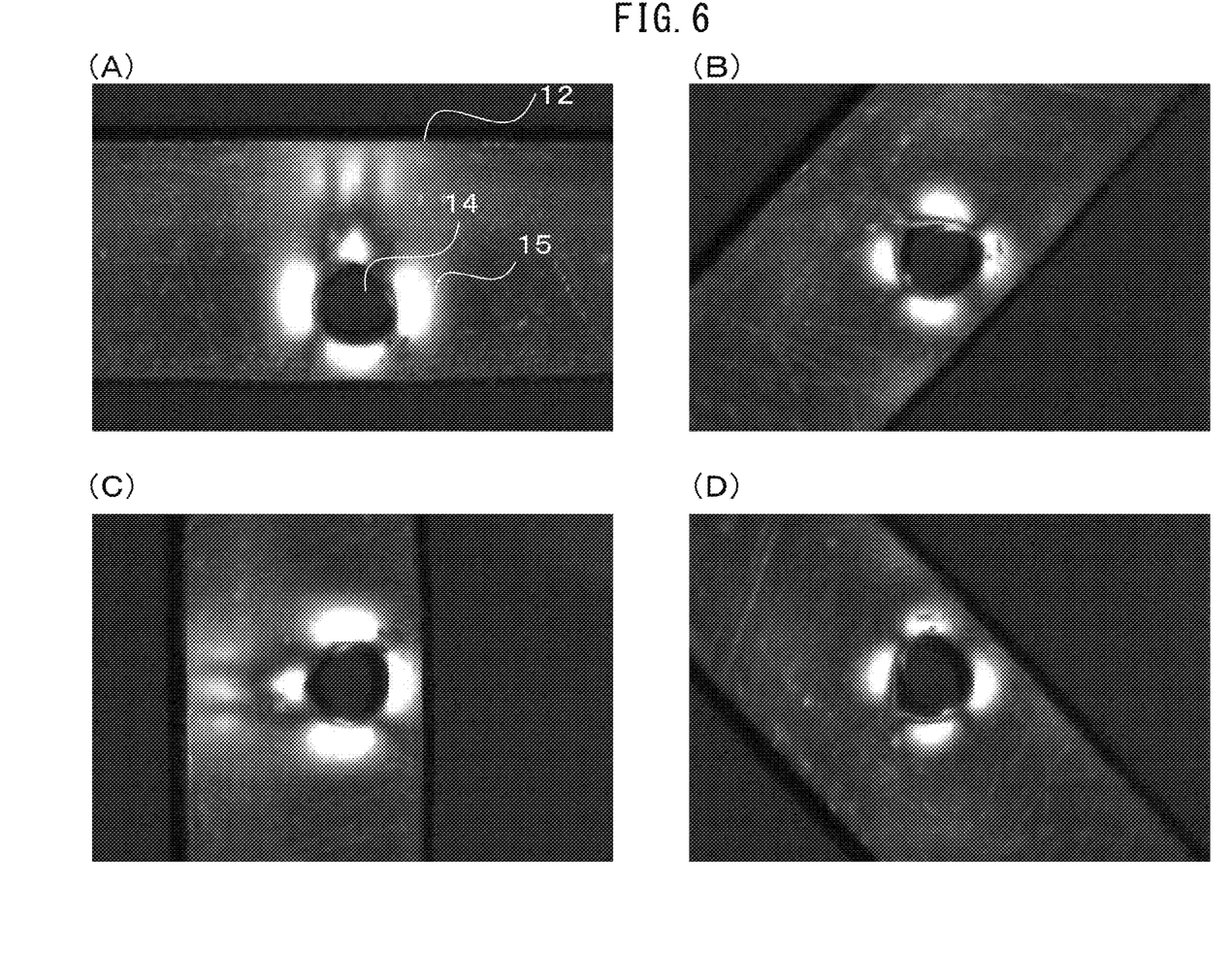
FIGS. 6(A) to (D) are photographs of cross sections of the optical element 10 perpendicular to the lengthwise direction thereof, observed by a polarizing microscope.
Figure 7:
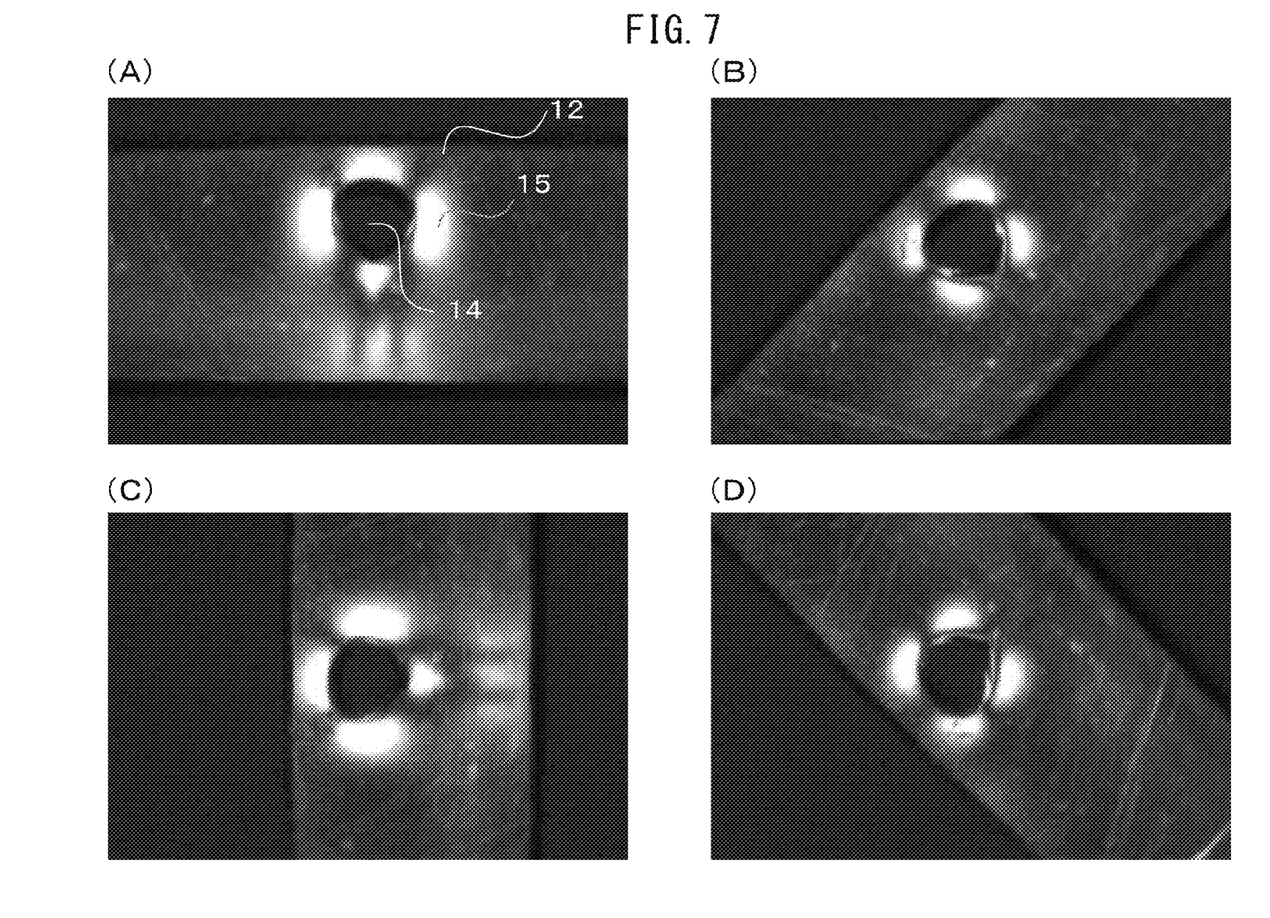
FIGS. 7(A) to (D) are photographs of cross sections of the optical element 10 perpendicular to the lengthwise direction thereof, observed by a polarizing microscope.

FIG. 5(A) to FIG. 5(D) are photographs of a plane, observed by a polarizing microscope, of the optical element 10 produced as described above parallel to the lengthwise direction thereof. FIG. 5(A) and FIG. 5(B) are photographs in which the angle of the lengthwise direction of the optical element 10 is 0° with respect to a polarizing plate angle of 45°. FIG. 5(C) and FIG. 5(D) are photographs in which the angle of the lengthwise direction of the optical element 10 is 45° with respect to a polarizing plate angle of 45°.

FIG. 5(A) represents the resin layer 12 into which the liquid crystal was allowed to penetrate with the channel 4A provided with the opening (not illustrated). In FIG. 5(A), the liquid crystal penetrates into the resin layer 12 and volatilizes, and the channel 4A is hollowed out. The liquid crystal region 15 outside the channel 4A is bright, revealing transmission of light. In addition, the liquid crystal penetrates to a depth approximately equal to the diameter of the channel 4A, revealing that there is a concentration gradient outside the liquid crystal region 15.

FIG. 5(B) illustrates the resin layer 12 into which the completely encapsulated liquid crystal 4 was allowed to penetrate. In FIG. 5(B), the liquid crystal 4 penetrates into the resin layer 12 and also remains in the channel 4A. It is found that light is transmitted not only in the liquid crystal region 15 outside the channel 4A but also in the channel 4A. Similarly to FIG. 5(A), the liquid crystal penetrates to a depth approximately equal to the diameter of the channel 4A, revealing that there is a concentration gradient outside the liquid crystal region 15.

FIG. 5(C) is a photograph of the resin layer 12 in FIG. 5(A), in which the lengthwise direction of the optical element 10 is inclined at an angle of 45°. The liquid crystal region 15, which transmits light when the angle of the lengthwise direction of the optical element 10 is 0° in FIG. 5(A), does not transmit light.

FIG. 5(D) is a photograph of the resin layer 12 in FIG. 5(B), in which the lengthwise direction of the optical element 10 is inclined at an angle of 45°. The channel 4A transmits light similarly to FIG. 5(B) in which the angle of the lengthwise direction of the optical element 10 is 0°, while the liquid crystal region 15 does not transmit light.

As described above, in either case of the hollowed-out channel and the channel in which the liquid crystal 4 remains, in the liquid crystal region 15 in the vicinity of the boundary with the channel 4A, light is transmitted when the angle between the polarizing plate and the lengthwise direction of the optical element 10 is 45°, while light is not transmitted when the angle between the polarizing plate and the lengthwise direction of the optical element 10 is 0°. Based on the above, it is found that the liquid crystal molecules penetrate with high orientation in the liquid crystal region 15.

FIG. 6(A) to FIG. 6(D) and FIG. 7(A) to FIG. 7(D) are photographs of cross sections of the optical element 10 produced as described above perpendicular to the lengthwise direction thereof, observed by a polarizing microscope. FIG. 6(A) to FIG. 6(D) and FIG. 7(A) to FIG. 7(D) are photographs of the optical element 10 rotated at 0°, 45°, 90°, 135°, 180°, 225°, 270°, and 315°, respectively.

As the resin layer 12, one having a channel with the interior thereof hollowed out was used similarly to FIG. 5(A). It is found that light is not transmitted to result in darkness only in the linear directions at 45° and 135° with respect to a horizontal line while light is transmitted in the other portions, in the liquid crystal region 15 in the vicinity of the boundary with the cavity 14, at each of the rotation angles. Since the pattern of the transmission is not changed depending on the rotation angle of the optical element 10, it is presumed that the liquid crystal molecules are oriented in an approximately radiating shape in the liquid crystal region 15.

The results of a waveguide simulation for investigating the polarization properties of the optical element 10 will be explained below. In this waveguide simulation, the electric field intensity of light propagated in each of rectangular regions in FIG. 8(A) and FIG. 8(B) with configurations similar to that of the optical element 10 was calculated using the FDTD method (finite difference time domain method).

Figure 8:
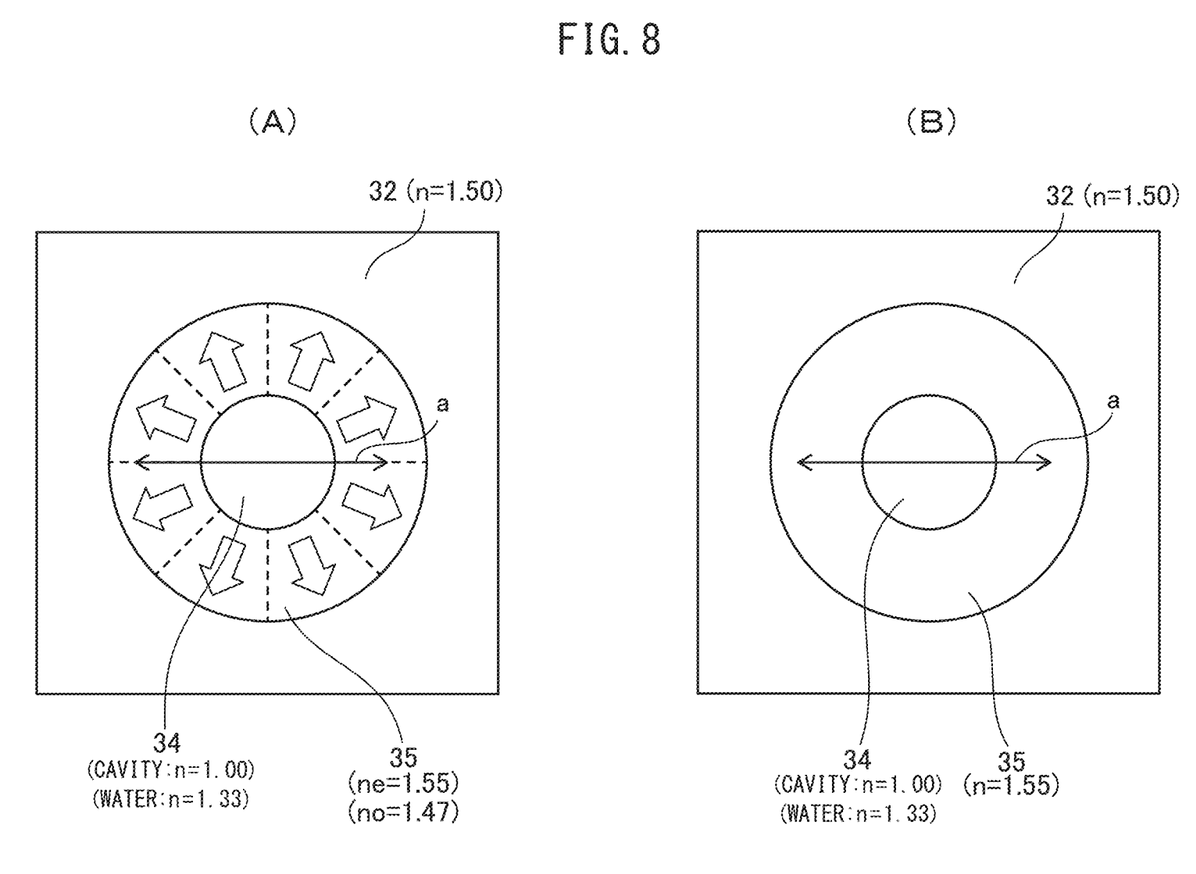

FIG. 8(A) and FIG. 8(B) are views for explaining the conditions of the waveguide simulation of the optical element 10. As illustrated in each of FIG. 8(A) and FIG. 8(B), the rectangular region targeted in the waveguide simulation includes a central region 34, an annular region 35 surrounding the central region 34, and an outer region 32 outside the annular region 35. The central region 34, the annular region 35, and the outer region 32 correspond to the cavity 14, the liquid crystal region 15, and the resin layer 12 in the optical element 10, respectively.

In the annular region 35 in FIG. 8(A), it was assumed that the major axis directions of the liquid crystal molecules were radially oriented and thus there was anisotropy, similarly to the optical element 10. The radial thick arrows in FIG. 8(A) represent the orientation directions of the liquid crystal molecules. On the other hand, in the annular region 35 in FIG. 8(B), it was assumed that the liquid crystal molecules were not oriented and thus there was isotropy, as a comparative example. In the outer regions 32, it was assumed that there was isotropy in both of FIG. 8(A) and FIG. 8(B).

The refractive index of the central region 34 was set at n=1.00 corresponding to the cavity (vacuum) or at n=1.33 corresponding to water, while the refractive index of the outer region 32 was set at n=1.50 corresponding to the acrylic resin. The settings of the refractive indices of the central region 34 and the outer region 32 were the same between FIG. 8(A) and FIG. 8(B). On the other hand, in the annular region 35 in FIG. 8(A), the extraordinary refractive index in the directions of the thick arrows was set at ne=1.55, while the ordinary refractive index in the directions perpendicular to the directions of the thick arrows was set at no=1.47. The refractive index of the annular region 35 in FIG. 8(B) was set at n=1.55.

In each of FIG. 8(A) and FIG. 8(B), a plane wave (TE wave) with a single wavelength, of which the polarization direction is the direction of an arrow a, was used as incident light.

Figure 9:
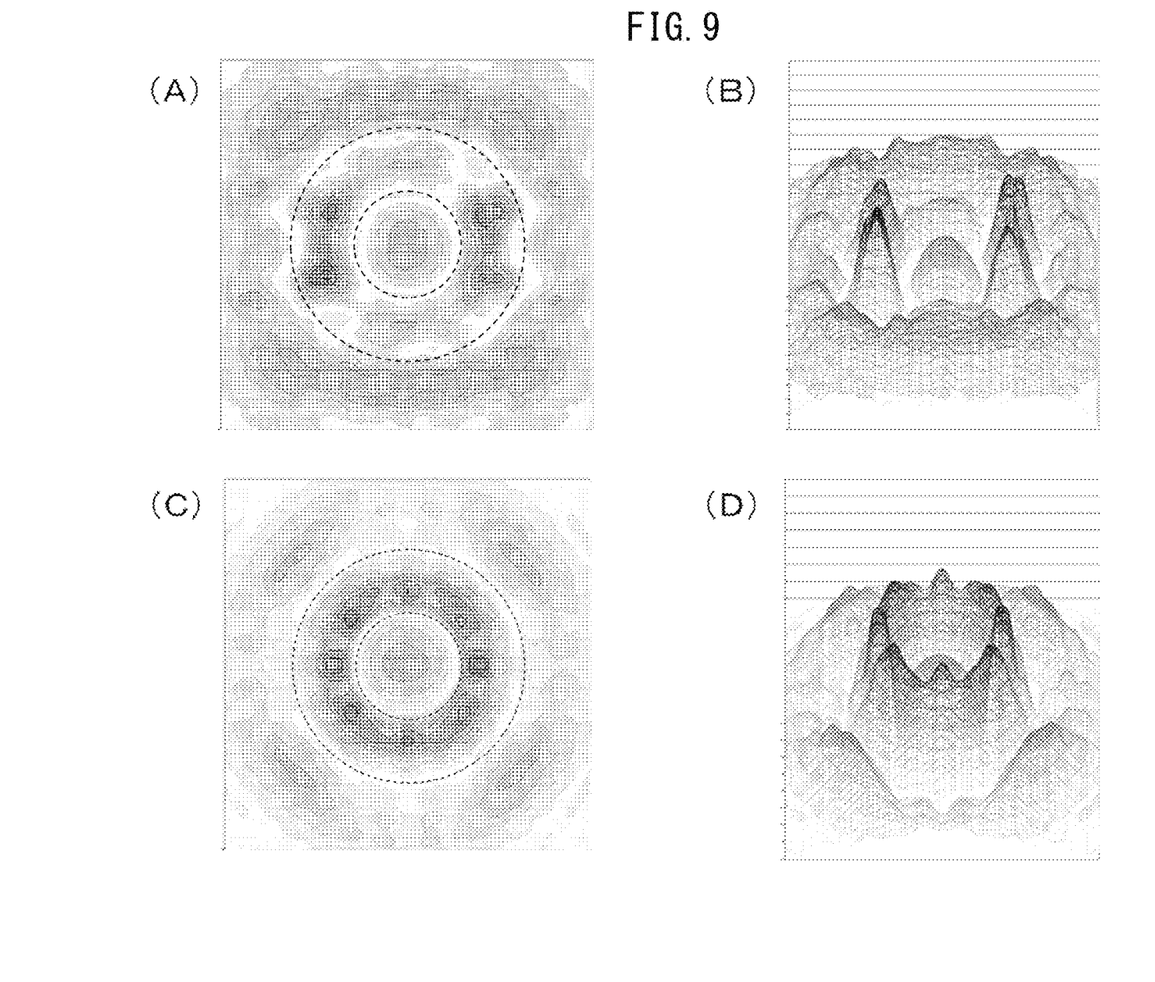
FIGS. 9(A) to (D) are views illustrating the results of a waveguide simulation in which the central region 34 is hollow.

FIG. 9(A) to FIG. 9(D) are views illustrating the results of a waveguide simulation in which the central region 34 is hollow. FIG. 9(A) and FIG. 9(B) represent the results on the conditions illustrated in FIG. 8(A), while FIG. 9(C) and FIG. 9(D) represent the results on the conditions illustrated in FIG. 8(B). In each figure, a point with higher electric field intensity is represented in a darker color, while a point with lower electric field intensity is represented in a lighter color. In FIG. 9(A) and FIG. 9(C), a portion corresponding to the annular region 35 is represented by broken lines.

As illustrated in FIG. 9(A) and FIG. 9(B), in the presence of orientation, the electric field intensity is the highest in the right and left portions of the annular region 35. In other words, it is found that light is confined in the annular region 35 having a high refractive index, and that light is guided particularly in the right and left portions of the annular region 35, in which the orientation direction of the liquid crystal molecules is parallel to the polarization direction (the direction of the arrow a in FIG. 8(A)) of incident light. In contrast, as illustrated in FIG. 9(C) and FIG. 9(D), in the absence of orientation, the electric field intensity is homogeneously high in the annular region 35. In other words, it is found that light is guided over the entire annular region 35 having a high refractive index.

When the liquid crystal molecules have orientation, the liquid crystal material of the present example has the effect of confinement of only polarized light in the direction parallel to the orientation direction thereof, and the polarized light is guided. Therefore, light can be guided while maintaining the polarization properties of radially polarized light in the optical element 10 including the liquid crystal region 15 in which the liquid crystal molecules are oriented in an approximately radiating shape. In other words, the extraordinary refractive index ne of the liquid crystal is 1.55, the ordinary refractive index no thereof is 1.47, the refractive index of the outer region 32 in FIG. 8(A) is n=1.50, and therefore, only the extraordinary refractive index ne of the liquid crystal is greater than the refractive index of the resin. Thus, only the eigenpolarization of extraordinary rays has a light confinement effect, and therefore, in this case, the light confinement effect resides only in radially polarized light.

Figure 10:
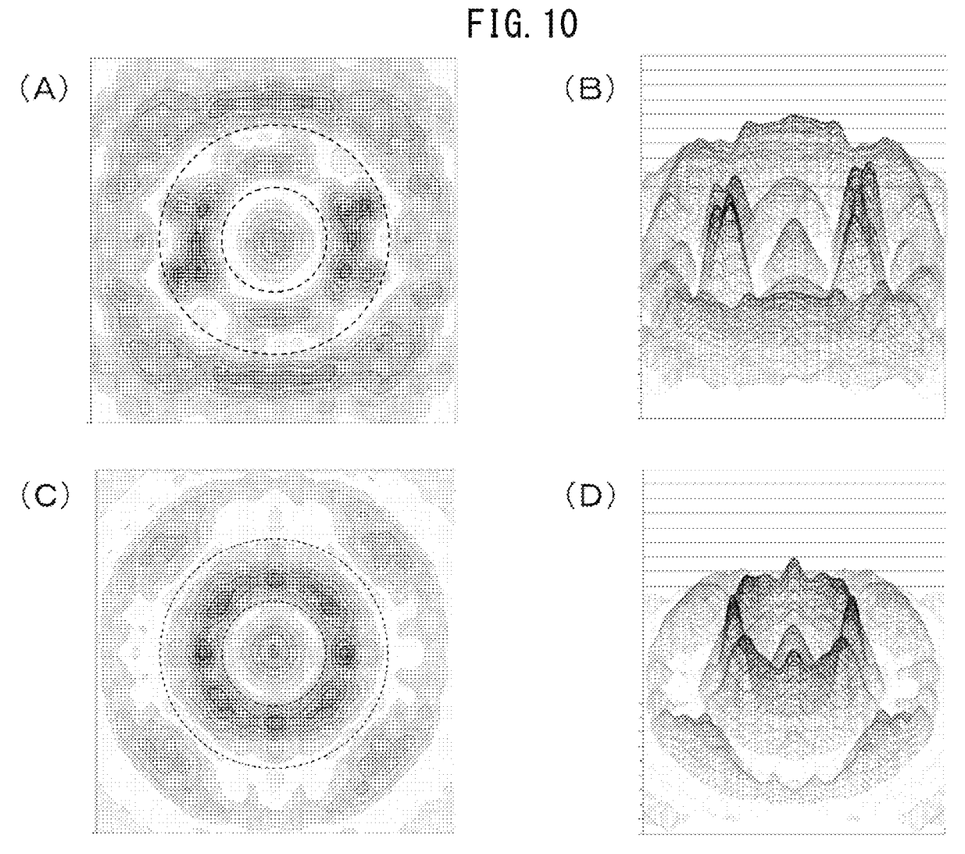
FIGS. 10(A) to (D) are views of the result of a waveguide simulation in the case of filling water into the central region 34.

FIG. 10(A) to FIG. 10(D) are views of the result of a waveguide simulation in the case of filling water into the central region 34. Similarly to FIG. 9(A) to FIG. 9(D), FIG. 10(A) and FIG. 10(B) represent the results on the conditions illustrated in FIG. 8(A), while FIG. 10(C) and FIG. 10(D) represent the results on the conditions illustrated in FIG. 8(B). In each figure, a point with higher electric field intensity is represented in a darker color, while a point with lower electric field intensity is represented in a lighter color.

In FIG. 10(A) and FIG. 10(C), a portion corresponding to the annular region 35 is represented by broken lines.

In FIG. 10(A) to FIG. 10(D), overall concentration differences are less than those in FIG. 9(A) to FIG. 9(D), and therefore, the function of the annular region 35 as an optical waveguide region is better than that in the case in which the central region 34 is hollow. However, even when the central region 34 is water (n=1.33), the magnitude relationship of the refractive index of each region is also equivalent to that in the case in which the central region 34 is hollow (n=1.00), and therefore, light is confined in the annular region 35 having a high refractive index, and tendencies similar to those in FIG. 9(A) to FIG. 9(D) are observed. In other words, light is guided in the right and left portions of the annular region 35 in FIG. 10(A) and FIG. 10(B) in the presence of orientation, while light is guided over the entire annular region 35 in FIG. 10(C) and FIG. 10(D) in the absence of orientation. Accordingly, the effect of guiding polarized light, similar to the effect obtained when there is a vacuum in the cavity 14, is also obtained when water flows in the cavity 14 of the optical element 10.

As explained above, the optical element 10 includes a structure in which the liquid crystal molecules are oriented in an approximately radiating shape along the radial direction of the approximately circular cross section of the cavity 14 which is a tubular space. As a result, the optical element 10 can propagate radially polarized light polarized along the orientation of the liquid crystal molecules while maintaining the polarization direction thereof. The optical element 10 can also propagate azimuthally polarized light polarized in a circumferential direction at an angle of 90° with respect to the liquid crystal molecules oriented in an approximately radiating shape in a radial direction while maintaining the polarization direction by using a liquid crystal material of which both extraordinary refractive index and ordinary refractive index are greater than the refractive index of a surrounding clad portion.

Finally, an application example of the optical element 10 will be explained. Application examples of the optical element 10 include, e.g., refractive index sensors (SPR sensors) utilizing a surface plasmon resonance phenomenon. The surface plasmon resonance is a phenomenon in which light with a wavelength and an angle depending on the refractive index of a medium in contact with a thin metallic film is absorbed when light is incident at not less than a total reflection angle on the inner surface of the thin metallic film which is in contact with the medium.

Figure 11:
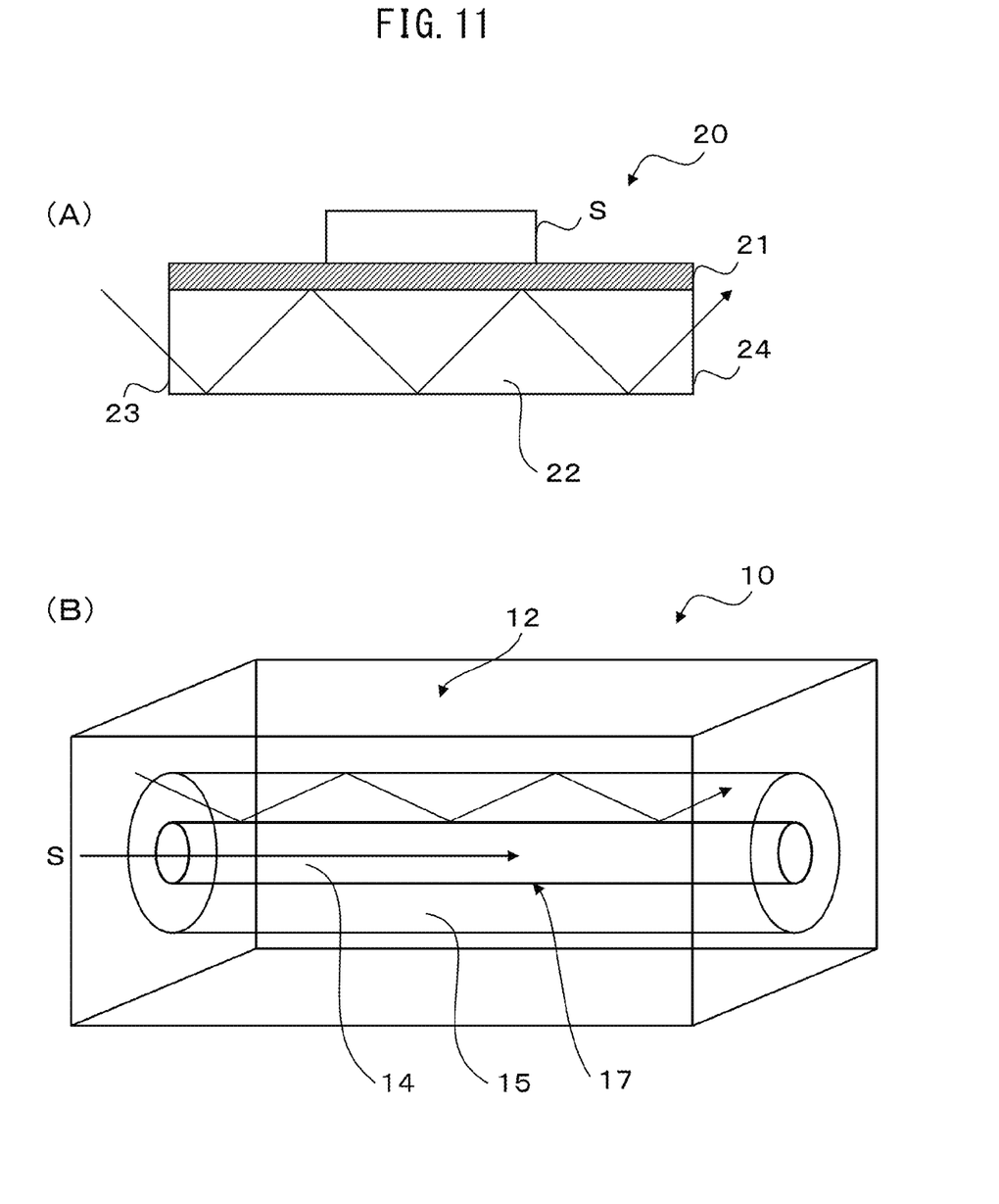

FIG. 11(A) and FIG. 11(B) are views for explaining an SPR sensor to which the optical element 10 is applied. FIG. 11(A) illustrates an example of a conventional waveguide-type SPR sensor 20. The SPR sensor 20 includes an optical waveguide 22 with a top surface on which a thin metallic film 21 is disposed. In measurement, a sample S targeted for the measurement is put on the thin metallic film 21, and light is introduced from an incidence plane 23 of the optical waveguide 22. The light is propagated while being repeatedly totally reflected in the optical waveguide 22, and is damped depending on the refractive index of the sample S. Therefore, a change in refractive index due to the sample S can be measured by detecting light emitted from an emission plane 24 and viewing the amount of transmitted light or the spectral change of the emitted light with respect to the incident light.

FIG. 11(B) illustrates a waveguide-type SPR sensor to which the optical element 10 in FIG. 1 is applied. The optical element 10 can be utilized as an SPR sensor by coating the inner wall of the cavity 14 with a thin metallic film 17, allowing a sample S to flow into the cavity 14, and allowing light to be propagated in the liquid crystal region 15 around the cavity 14. By coating the cavity 14 with the thin metallic film 17, the whole boundary surface between the cavity 14 and the liquid crystal region 15 can be used as a sensor, and therefore, the surface area of the sensor is larger than that of the SPR sensor 20 described above. Thus, the SPR sensor in which the optical element 10 is used can measure a more sensitive change in refractive index in proportion to the area ratio of the sensor. In particular, the sensitivity of the SPR sensor can be improved by utilizing the orientation of liquid crystal molecules in the liquid crystal region 15 to control the polarized light of light incident on the thin metallic film 17 which is a sensor portion.

REFERENCE SIGNS LIST 10 optical element
12 resin layer
14 cavity
15 liquid crystal region
16 boundary surface

What is claimed is:

1. An optical element comprising:
   a resin layer; and
   an optical waveguide region that is formed in the resin layer and guides light in the lengthwise direction of the resin layer,
   wherein liquid crystal molecules are oriented in an approximately radiating shape in a cross section perpendicular to the lengthwise direction in the optical waveguide region, and
   the refractive index of the optical waveguide region is greater than that of the resin layer.

2. The optical element according to claim 1, further comprising a tubular space having an approximately circular cross section formed in the resin layer,
   wherein the optical waveguide region is formed so as to be in contact with the tubular space, and
   liquid crystal molecules are oriented in an approximately radiating shape along the radial direction of the approximately circular cross section in the optical waveguide region.

3. The optical element according to claim 1, wherein the resin layer is an acrylic resin layer, and the liquid crystal is a P-type liquid crystal.

4. The optical element according to claim 2, wherein the resin layer is an acrylic resin layer, and the liquid crystal is a P-type liquid crystal.

* * * * *